(12) United States Patent
Goldenberg (10) Patent No.: US 7,934,495 B2
(45) Date of Patent: May 3, 2011

(54) CONTROLLED MECHANICAL HEATING—WAX SKIN THERAPY AND AROMATHERAPY (75) Inventor: Michael Goldenberg, Brooklyn, NY (US)

(73) Assignee: Rachel Goldenberg, Brooklyn, NY (US)

(*) Notice: Subject to any disclaimer, the term of this patent is extended or adjusted under 35 U.S.C. 154(b) by 1494 days.

(21) Appl. No.: 11/284,019

(22) Filed: Nov. 21, 2005

(65) Prior Publication Data
US 2007/0117059 A1 May 24, 2007

(51) Int. Cl.
A61L 9/03 (2006.01)
A47G 23/04 (2006.01)
A61L 9/02 (2006.01)

(52) U.S. Cl. ............... 126/343.5 R; 126/208; 126/45; 126/281; 126/282; 126/284; 126/46; 126/47; 126/49; 607/114

(58) Field of Classification Search ............. 126/208, 126/265, 261, 260, 43, 262, 281, 282, 284, 126/343.5 R; 374/141, 150, 157, 159
See application file for complete search history.

(56) References Cited

U.S. PATENT DOCUMENTS

| 26,957 | A | * | 1/1860 | Turner | 126/284 |
|---|---|---|---|---|---|
| 47,749 | A | * | 5/1865 | Reynolds | 126/208 |
| 60,032 | A | * | 11/1866 | Mellinger | 126/208 |
| 152,504 | A | * | 6/1874 | Miller | 126/260 |
| 208,251 | A | * | 9/1878 | Mains | 126/265 |
| 371,702 | A | * | 10/1887 | Parkhill | 126/282 |
| 510,536 | A | * | 12/1893 | Grush et al. | 126/282 |
| 611,560 | A | * | 9/1898 | Chambers | 422/125 |
| 725,335 | A | * | 4/1903 | Glaessner | 126/43 |
| 877,349 | A | * | 1/1908 | Little | 126/265 |
| 1,043,674 | A | * | 11/1912 | Craig | 126/266 |
| 1,090,056 | A | * | 3/1914 | Hildum | 126/266 |
| 1,437,812 | A | * | 12/1922 | MacMillan | 126/38 |
| 1,485,292 | A | * | 2/1924 | Popper | 422/300 |
| 1,739,138 | A | * | 12/1929 | Giragosian | 126/344 |
| 2,581,131 | A | * | 1/1952 | Naranick | 126/262 |
| 2,584,040 | A | * | 1/1952 | Naranick | 126/262 |
| 2,641,246 | A | * | 6/1953 | Guthof | 126/275 R |
| 2,660,060 | A | * | 11/1953 | Shelton | 374/150 |
| 2,666,060 | A | * | 1/1954 | Hoffmann et al. | 546/187 |
| 2,671,330 | A | * | 3/1954 | Ajello | 431/146 |
| 2,678,644 | A | * | 5/1954 | Banks et al. | 126/261 |
| 2,829,635 | A | * | 4/1958 | Teller | 126/208 |
| 2,845,924 | A | * | 8/1958 | Benda | 126/208 |
| 3,024,782 | A | * | 3/1962 | Knopps | 126/208 |
| 3,093,129 | A | * | 6/1963 | Pickard, Jr. | 126/65 |
| 3,144,015 | A | * | 8/1964 | Jankowski | 126/261 |
| 3,327,505 | A | * | 6/1967 | Brown | 431/288 |
| 3,428,410 | A | * | 2/1969 | Huddleston et al. | 431/291 |
| 3,566,857 | A | * | 3/1971 | Price | 126/262 |

(Continued)

FOREIGN PATENT DOCUMENTS

DE 10306878 A1 * 7/2004

(Continued)

Primary Examiner — Carl D Price
(74) Attorney, Agent, or Firm — Israel Nissenbaum (57) ABSTRACT A non-thermostatic heating device is provided with temperature range control whereby materials may be heated and melted to a safe or desired temperature and maintained, particularly soy based non-candle formulated waxes for skin therapy as well as aromatherapy waxes generally. The device is vented and comprises a non flammable insulative container such as treated paper tubing and semi insulative elements, particularly one or more enclosed air pockets which are predetermined in dimension or movable for change in volume to provide a desired equilibrium temperature range.

9 Claims, 4 Drawing Sheets

U.S. PATENT DOCUMENTS

| | | | | |
|---|---|---|---|---|
| 3,613,658 | A | * | 10/1971 | Knowles et al. ............... 44/275 |
| 3,637,335 | A | * | 1/1972 | Uhl ............................. 431/291 |
| 3,682,154 | A | * | 8/1972 | Mollere ....................... 126/9 A |
| 3,727,979 | A | | 4/1973 | Schier et al. ............. 297/440.12 |
| 4,304,547 | A | * | 12/1981 | Buzil ............................ 431/126 |
| 4,432,338 | A | * | 2/1984 | Buchmann .................... 126/256 |
| 4,564,299 | A | * | 1/1986 | Ehrenkranz .................. 374/157 |
| 4,676,223 | A | * | 6/1987 | Peterson ....................... 126/208 |
| 4,781,895 | A | * | 11/1988 | Spector ........................ 422/125 |
| 4,784,112 | A | * | 11/1988 | Hayashi ........................ 126/262 |
| 4,907,140 | A | * | 3/1990 | Overstreet .................... 362/162 |
| 5,197,454 | A | * | 3/1993 | Lee ............................... 126/9 R |
| 5,366,491 | A | * | 11/1994 | Ingram et al. ................. 607/108 |
| 5,827,483 | A | * | 10/1998 | Fullam .......................... 422/122 |
| D402,201 | S | * | 12/1998 | Miller ............................ D9/431 |
| 6,280,753 | B1 | | 8/2001 | Chung |
| 6,354,710 | B1 | | 3/2002 | Nacouzi |
| 6,627,072 | B1 | | 9/2003 | Ridge |
| 6,669,468 | B2 | | 12/2003 | Pesu |
| 6,700,100 | B2 | * | 3/2004 | Lerner ........................ 219/445.1 |
| 2005/0178773 | A1 | * | 8/2005 | Sena et al. ..................... 220/703 |
| 2005/0238775 | A1 | * | 10/2005 | Amodei ......................... 426/520 |
| 2007/0117059 | A1 | * | 5/2007 | Goldenberg .................. 431/289 |

FOREIGN PATENT DOCUMENTS

| | | | |
|---|---|---|---|
| GB | 2252026 A | * | 7/1992 |
| GB | 2310145 | * | 8/1997 |
| WO | WO 9717996 | * | 5/1997 |

* cited by examiner

CONTROLLED MECHANICAL HEATING—WAX SKIN THERAPY AND AROMATHERAPY

FIELD OF THE INVENTION

This invention relates to controlled mechanical heating particularly of non-candle waxes and particularly soy based waxes (hydrogenated soy oil), for aromatherapy and for heated wax skin treatment with non-thermostatically controlled heating devices.

BACKGROUND OF THE INVENTION

Many substances require heating for proper use and often the heating must be to a controlled temperature. Poaching or boiling with water is a most common controlled method of heating because of the specific temperature at which water boils prior to vaporization (100° C., 212° F.). However, in order to control heating temperatures (i.e. maintenance of temperatures at specified levels) at other than the water boiling temperature, heating devices are used, invariably with thermostatic controls which turn the heat on and off to maintain a constant temperature. Electric and gas heaters are most often provided with thermostats which control the current and valve flow respectively, to control heat intensity and thus maintain a pre-determined temperature. With sources of heat such as candles and the like, thermostatic control of the heat intensity and thus temperature control is not a readily viable option.

An example of candle heat application requiring at least a modicum of temperature control is that of heating substances for aroma generation such as waxes with fragrance components which are released only with heat. Excessive heating may be detrimental (with excessive aroma generation) but no appropriate temperature control is commonly used or even commonly known.

Waxes, for their various utilities, require heated melting. Waxes are solidified viscous, usually burnable materials (e.g., paraffin, fats and hydrogenated oils such as soy wax) which have historically been used for illumination as taper candles. At present, more commonly, the waxes, with fragrance additives, are used for providing a pleasing or masking ambient aroma (aromatherapy). The wax is used in candles or as non-candle pellets, blocks or as glass container fillings, heated by a secondary source of heat, to release the aroma.

Another common use of ingredients found in waxes, is ambient temperature skin treatment such as soaps, lotions and the like, most often with a soy oil component. Lotions, in liquid form, however generally can only contain relatively minor amounts of soy derivatives and complexes in liquid carriers.

Some actual waxes are however used at higher temperatures, at which they are melted and used for skin application in heated form such as paraffin dips. Depilatory waxes are also often warmed prior to use. Care must however be taken with such applications to constantly maintain temperature control since overheating will detrimentally scald the user's skin. These waxes are heated and melted either in thermostatically controlled devices or are heated to the point of melting and the heat source is removed. With the latter embodiment, the wax must be quickly utilized before it resolidifies. Paraffin baths must be kept at a very narrow low heat range (123° F. to 129° F.) because of full limb immersion with little heat loss.

Melted soy wax of some soy based candles has been touted as being beneficial for skin application. The melted soy wax (sometimes with other skin beneficial ingredients) is taken from pools of the melted soy wax surrounding the candle wick, after the candle has been extinguished, and before the heated candle material has had a chance to cool and solidify, i.e., a short window of possible use without continued heating (unless the candle is re-lit). Additionally, much of the candle wax available for skin application may be lost by fuel consumption if the candle is allowed to continue burning.

Non-candle waxes used in aromatherapy are usually small pellets or larger blocks without wicks which are heated with candle warmers. These candle warmers are generally comprised of hollow or open ceramic or glass containers or stands with an upper dished portion for placement of the pellets or blocks of the aromatherapy wax. Commonly, a tea light candle is placed within the container or below the dished portion for providing the heat for melting the wax and releasing the fragrance. Over time (often within thirty minutes) the wax melts and puddles within the dished portion and, despite extensive ventilation of the container with vent apertures, the wax may reach temperatures of 250° F. and above since temperature control of candle generated heat is not readily feasible. At such temperatures, the container cannot be readily handled except with heat insulated materials and the released fragrance can become excessive, overpowering and even toxic. Alternatively, electric heaters, without temperature control, akin to coffee cup warmers, are utilized to provide the requisite heating. Again, this may lead to excessive heating levels (or inadequate heating and utility) As referred to above, waxes used for skin treatment or skin therapy include melted paraffin dips or baths wherein a user dips a hand, foot or other body part therein with the wax hardening upon removal of the body part from the bath and the hardened wax is removed by being peeling off. The bath is almost always an electric device with a thermostatic control (a temperature sensitive element which controls the heat reaching the contents) to ensure that the paraffin does not overheat and scald the user. The paraffin itself however, has little particularly significant beneficial effect on the skin except for the effect of the imparted heat or warmth since it is not skin absorbable and is only a skin surface treatment. Since it is organic and non soluble, paraffin is also difficult to remove from skin and fabrics. A recent paraffin wax treatment eschews electrical heating (or heating with a microwave) and utilizes an exothermic reaction with water to heat the paraffin to the desired temperature of 122° F. and maintaining it by insulation in a sealed glove or slipper.

Soy derivatives and waxes on the other hand have been found to be beneficial to skin, with lotions of soy complexes being absorbed into the skin with improvement in the appearance of skin tone, softening and smoothing skin texture, and moisturizing dry skin areas. In addition, soy based waxes are water soluble and are easy to remove by simple washing. Various manufacturers have therefore formulated lines of soy based non-wax lotions for use in skin care. Such lotions are however used at ambient temperatures with relatively minimal soy oil content and do not have the added benefit of being applied to pores opened with heat. To take advantage of the benefit of heated soy wax as a skin application, soy based wax candles have been marketed specifically, as described above, for the application of soy containing wax at elevated temperatures. With such candles the users are instructed to extinguish the flame after the soy wax has melted and to use the melted material for topical skin application. However, there remains the constant danger that the user will not extinguish the flame and will be burned. In addition, the topical application and use is within a short window of time before the soy based wax re-solidifies. The candle wax also objectionably retains a burnt aroma from having initially been used as a candle fuel.

In any event, the most disadvantageous feature of such candles is the inclusion of combustion enhancing skin adverse additives. Soy oil or wax in itself has an unpleasant odor making it unsuitable for skin application without the further inclusion of masking fragrances. However, many normal fragrances used with the soy based lotions are unsuitable for candle use since they impede proper candle burning. Furthermore, many fragrances which do support a properly burning candle flame are not acceptable under FDA and IFRA standards for skin application, either in any amount or in the amounts used in candles, and any benefit achieved by heating the soy based material is lost by toxicity engendered by the necessarily added unapproved fragrances. Examples of fragrances suitable for candles include IFF fragrance designated Juicy Orange which is only recommended for candle use and not skin lotion use. IFF Zesty Grapefruit fragrance is recommended for both candle and lotion use but with the former at levels of 3-6% whereas for the latter, the maximum is 3%. At present, wax heating of skin suitable waxes is via candle wax residue, as described, or by means of electrical thermostatic controlled heaters such as used for paraffin baths.

SUMMARY OF THE INVENTION

It is therefore an object of the present invention to provide inexpensive non-thermostatic heating control for substances requiring heating and particularly for use with substances producing aromas such as aromatherapy waxes and for heating substances such as waxes for use in skin therapy.

It is a further object of the present invention to provide a method for safely utilizing soy based waxes (with at least 70% by weight of soy components) as heated topical application material for skin care without non skin approved additives, and optionally with the inclusion of skin or cosmetic approved additives.

It is yet another object of the present invention to provide non-thermostatic mechanical heating devices for safe controlled heating of non-candle waxes formulated for aromatherapy and non-candle soy based waxes for skin treatment.

It is still another object of the present invention to provide said heating devices with non thermostatic temperature control means to maintain heating therewith of soy based waxes at skin tolerated temperatures during heating use.

It is another object of the present invention to provide the heating device with control means to quickly obtain a melting or desired temperature and then to maintain a desired melting temperature as an equilibrium temperature in an equilibrium temperature range.

It is yet still another object of the present invention to provide said devices with temperature sensitive changeable indicia means to advise a user of excessive wax heating and/or when to establish an equilibrium temperature and/or range.

It is another object of the present invention to provide the heating device with means for providing an aesthetically pleasing ambient appearance and illumination and which effects more efficient candle burning.

Generally the present invention comprises a method for the use of heated non-candle formulated soy based wax (without skin adverse fragrance additives) as a skin treatment at a temperature between about 115° F. and 150° F. and preferably at temperature at which the soy based wax becomes viscous, to a maximum temperature of 140° F. and most preferably between about 125° F. to about 135° F. (without immersion, somewhat higher temperatures are comfortably tolerated compared to paraffin baths) or, the range at which skin pores open for maximum safe absorption. In a preferred embodiment of the present invention, the non-candle soy based wax is heated with a mechanical device comprising non-thermostatic temperature control means suitable for attaining and maintaining the above temperatures or temperature ranges. The term "non-candle" encompasses materials and waxes from which candle enhancing materials, which are not acceptable for skin use, have been excluded.

The present invention further comprises a mechanical non-thermostatic heating device which enables the effective use of the non-candle soy wax, though its use is effective with any application requiring mechanical heat control. The device comprises an insulative flame retardant container (the term "container", as used herein, is with respect to the containment of a heat source such as a tea light) with a bottom closure, and an upper closure comprised of semi insulative-semi heat-conductive means. The soy wax used for skin treatment, or the aromatherapy wax, or any other material requiring melting or heating, is placed on top of the container closure within a dished section adapted to contain the wax when puddled (alternatively, the wax is contained and melted within its own heat conductive container within the dished section). The container further comprises non-thermostatic heat control means with said heat being generated by a candle flame, electric heating element, gas flame and the like, situated within (or below, since heat rises) said container. The non-thermostatic control means primarily comprises, for example, any or all of the following mechanical considerations and variables:

1) The temperature of the heat source, e.g., paraffin candles or tea lights burn at a temperature of 1000 to 1200° F. whereas soy based candles or tea lights burn at a lower temperature of 700 to 800° F. Wick width and type (paper core burns hotter and pure cotton burns cooler are wicks which are used with soy based candles) further adjusts the burning temperature within the range. Larger wicks such as a Wick-it #725 wick, provide a large flame and hotter temperature and a #710 or #715 wick provides a significant reduction in flame size and lower temperature and is preferred for better heat control (the #725 wick is a common one used in tea lights). Other heat sources typically have their own known heat source temperatures;

2) The distance between the heat source and the upper closure with contained substance to be heated such as candle flame, the further the distance the lower the heat. An excessive distance can however vitiate effective use, with substance melting being unacceptably delayed;

3) The extent of venting means such as the size and number of apertures in the container walls (or even completely open sides), for dissipation of heat, with increase in the total area of venting serving to reduce the equilibrium temperature obtained;

4) The distance between the apertures and the top closure (i.e., areas of trapped heat), with the lesser the distance the lower the amount of trapped heat and the lower the temperature;

5) The cross section areal and volumetric dimensions of the container, with concomitant heat retention, with the greater the areal or volume dispersal the lower the concentration of heat and the lower the obtained temperature;

6) The number and extent of heat insulation/conduction closure members or the use of adjustable movement means, with each additional closure member and enclosed air volume, increase in insulation value (R factor) or increase in volume of the enclosed air reducing the obtained equilibrium temperature; and 7) The nature of the container walls with respect to heat retention/transmission levels and internal heat reflection.

The present invention further comprises a method for heating a substance having characteristics operable at or having utility at a specific temperature range, (such as aromatic or skin therapy waxes), to the specific temperature range and maintaining it as a controlled equilibrium temperature range, the method comprising the steps of: placing a substance such as a wax composition on a hollow, vented container comprised of a non flammable insulative material and having an upper heat conductive receptacle for the substance, placing a heat source such as a candle flame within the container for heating of the substance, and providing the container with non-thermostatic temperature control means whereby the temperature of the heated substance is maintained at a predetermined equilibrium temperature range suitable for a selected substance use. For skin therapy the predetermined temperature range for a soy containing wax is preferably from wax melting temperature of about 115° F. to about 140° F. and for aromatherapy it is preferably between about 120° F. to 180° F.

The present invention further comprises the vented container, non-thermostatic controlled heating device. The container is adapted to contain a candle, preferably a tea light and to support a wax material above the candle and the heat generated therewith. The container device further comprises mechanical temperature control means for regulating the temperature with a partially insulative element situated between the interior of the container device, with contained tea light, and the wax being heated. The partially insulative element is adapted to permit heat therethrough with increasing temperature elevation sufficient to melt the wax until a desired equilibrium temperature or temperature range is reached and maintained. For skin therapy wax application, the desired temperature equilibrium is in the range of between about 120° F. to 140° F. (sufficient to melt the wax but not sufficient to be uncomfortable or scald the user). For aromatherapy purposes the equilibrium temperature range is between 120° F. to about 180° F. (sufficient to melt the wax and release the aroma but not above a temperature which would degrade or burn the wax or overheat the container whereby it could not be safely handled or moved), preferably not to a temperature above 160° F. Aromatherapy waxes are typically formulated to melt at higher temperatures (since skin contact temperature is not a factor) to prevent melting during shipment when the waxes may be subjected to elevated temperatures.

Factors of ambient conditions, the size of the container, the degree of venting (size and number of apertures in the container), the material composition of the container and the degree of insulation and heat conductance are variable factors which are balanced to provide the requisite equilibrium temperature control. In one embodiment of the present invention, the mechanical temperature control means are predetermined to provide a predetermined operable equilibrium temperature range. In another embodiment of the present invention means are provided to vary one or more of the above factors to enable controlled varying of an operable temperature and the maintained equilibrium temperature.

The above and other objects, features and advantages of the present invention will become more evident from the following discussion and drawings in which:

DETAILED DESCRIPTION OF THE INVENTION

The present invention has particular application in allowing the safe and effective utilization of soy based wax (at least 70% and preferably at about 90% by weight or more) as a heated lotion with all the attendant skin therapy benefits. With the mechanical heat control device of the present invention the wax is maintained at a safe melted temperature without the drawbacks of candle waxes. There is no burnt smell and any skin acceptable fragrance may be utilized in the soy formulation. Since pure soy waxes have an objectionable scent it is necessary for consumer acceptance to formulate the wax with a fragrance. This is of course necessary for aromatherapy by definition and is highly desirable for skin care applications as well. Soy waxes formulated for candle use as well as skin care use are limited to the highly restricted formulations which are both acceptable for candles and for skin. To date, skin acceptability has often been sacrificed to the more visible candle acceptability.

Hot melt soy wax formulations, as described, contain at least 70% soy components. Ideal soy waxes which are mixed with fragrances and other components include Golden brands pure soy blend formulations 402, 415 and 416. This is in contrast to soy complexes and lotions used at ambient temperatures which contain far less soy components. Other materials which may be added to the soy formulation used for the hot melt application of the present invention include Shea Butter, Cocoa Butter, Sweet Almond Oil, fragrances (as described), Beeswax and Green Tea Extract, with each having specific utilities such as moisturization, vitamin and protein addition, anti-oxidant activity, anti-inflammatory effect, etc. Many other additives are also available for inclusion as desired. It is understood that a soy wax with a wick and utilizable as a candle but which is otherwise acceptable for skin application is within the purview of the present invention.

Regardless of the formulation of the waxes, the heating device of the present invention heats and maintains them within the requisite heat utility range for maximum effective absorption.

A container suitable for maintaining soy based waxes at a useful heated skin application range of between 120-140° F. comprises an approximately three inch diameter non-flammable compressed non flammable paper tube of structural integrity with about a four inch height and with three cutouts arranged around the perimeter of the tube and spaced equidistantly. The cutouts are each approximate ovals or ellipses longitudinally positioned within ½ inch of the upper rim (aesthetically the cutouts are in a design such as a leaf with about 1.5" and 2.5" major and minor axes). Reducing the height to 3 and ¼ inches and with only two cutouts modifies the equilibrium temperature to about 160-180° F., suitable for aromatherapy utilization.

In a preferred embodiment of the present invention, the heating container comprises a compressed paper tube having a reflective metallic inner coating (thin aluminum foil) into which a tea light is placed. Compressed paper which is impregnated with chemical flame retardants is not flammable, is not heat conductive and does not distort with heat as do many plastic compositions. Other flame retardant materials, such as ceramics, glass, and metal tend to continue being heated and present a hot exterior and are less preferred. Among many sources, ideal paper tubes are for example, available from the Jonesville Paper Tube Corp., Jonesville, Mich. as di-electric neutral kraft insulative tubes used for electrical equipment which are treated for flame retardancy.

In accordance with the present invention, the tube is then aperture vented around its periphery, preferably with decorative apertures such as leaf designs, with the apertures extending close to the upper open end. The tube has sufficient structural integrity to function as a container rather than as a supported enclosure.

The paper tubes with apertures and internal reflective surface may be used without top and bottom as open ended cylinders or sleeves to slip onto glass cylinders containing candle wax. The reflection of heat by the internal reflective surface serves to more uniformly utilize the candle wax and permit lower candle temperatures. The wick size, normally increased to provide uniform candle burning (but with concomitant temperature increase) can be reduced with maintained uniform candle burning.

The open upper end is fittingly closed with a metallic cup (commercially available as tinned stainless steel) of a diameter slightly less than the three inches of the paper tube and a height of about ¾" and having a retaining lip for positive engagement seating with the end of the tube cylinder. The apertures permit air access to the enclosed tea light and permits excessive heat to vent. Since heat rises and is trapped in the upper portion of the tube extending the height of the apertures close to the metallic cup cap provides for maximum heat venting. Though it is not preferred, it may be possible to slip tea lights into the container through the leaf cutouts of the size described.

In the construction of an embodiment of the present invention a second tube element of about 1 and ¼ height and a diameter slightly less than that of the cup is placed into the tin cup and a second cup, appropriately dimensioned is used to close the upper open end of the second tube element and to contain the soy wax formulation for skin or aromatherapy. The second cup, for skin therapy purposes, is preferably preloaded with the skin therapy wax (in pellets or a single block) and is comprised of an acceptable metal such as aluminum, for use with skin application materials. In such configuration there is an insulating trapped air volume between the cups and bounded by the second tube element with an overall dimension of slightly less than 3" diameter and an interior height of about ¾" (the height of the second tube less the ¾" of the nested second cup. With a total height of about 3.75" and a contained tea light with a #715 wick and two leaf cutouts, the equilibrium temperature does not exceed 180° F. and with ideal ambient conditions, the temperature range is between 150-160° F. This is a heating device suitable for aromatherapy use. With three cutouts and a total height of about 4.75 inches, the temperature does not exceed about 150° F. and with ideal ambient conditions the temperature range is between 125-135° F., making it suitable for use in skin therapy with soy waxes. It is understood that temperatures may vary somewhat with consideration of the various factors enumerated above as well as ambient conditions.

In order to attain a lower equilibrium temperature by about 10-20° F., a second inverted tinned cup is placed into the first cup to provide an additional insulating air volume. For maintaining cup integrity, the cups in more direct contact with the heat source are preferably tinned steel whereas a more inert metal such as aluminum is acceptable as being in direct contact with a heated substance used for skin application.

The formation of enclosed air spaces by conductive metallic cup elements provides semi-conductive heat transfer elements which can be closely controlled. Each cup section of standard size tins enclosed an air insulation volume sufficient to reduce temperature of the heated wax by about 10 to 20° F.

Alternatively and more preferably the device comprises means for allowing the user to vary the distance (and concomitantly the equilibrium temperature) between the heat source and the substance to be heated. An example of this embodiment includes the first cup but with the second tube element being larger in diameter and sized to snugly fit and be moved on the outside of the first tube, whereby the volume between the lower cup and the cup supported by the second tube is changeable with raising of the outer tube serving to almost instantly drop the equilibrium temperature and lowering of the second tube serving to raise the equilibrium temperature. With this embodiment it is possible to initially accelerate heating by lowering the outer tube and then, when indicia of melting is obtained, the outer tube is raised until an equilibrium temperature is obtained and maintained. The cup containing the wax (or other material to be heated) is preferably sealingly adhered to the second tube to provide a more air tight seal whereby a greater vacuum is formed by raising of the second tube with the ingress of cooler air in the defined volume.

In all embodiments, the tea light is contained within a heavy support stand within the container (about 5 ounces for a glass stand as opposed to the one ounce weight of container), whereby the possibility of container tipping is minimized.

DETAILED DESCRIPTION OF THE DRAWINGS AND THE PREFERRED EMBODIMENTS

Figure 1:
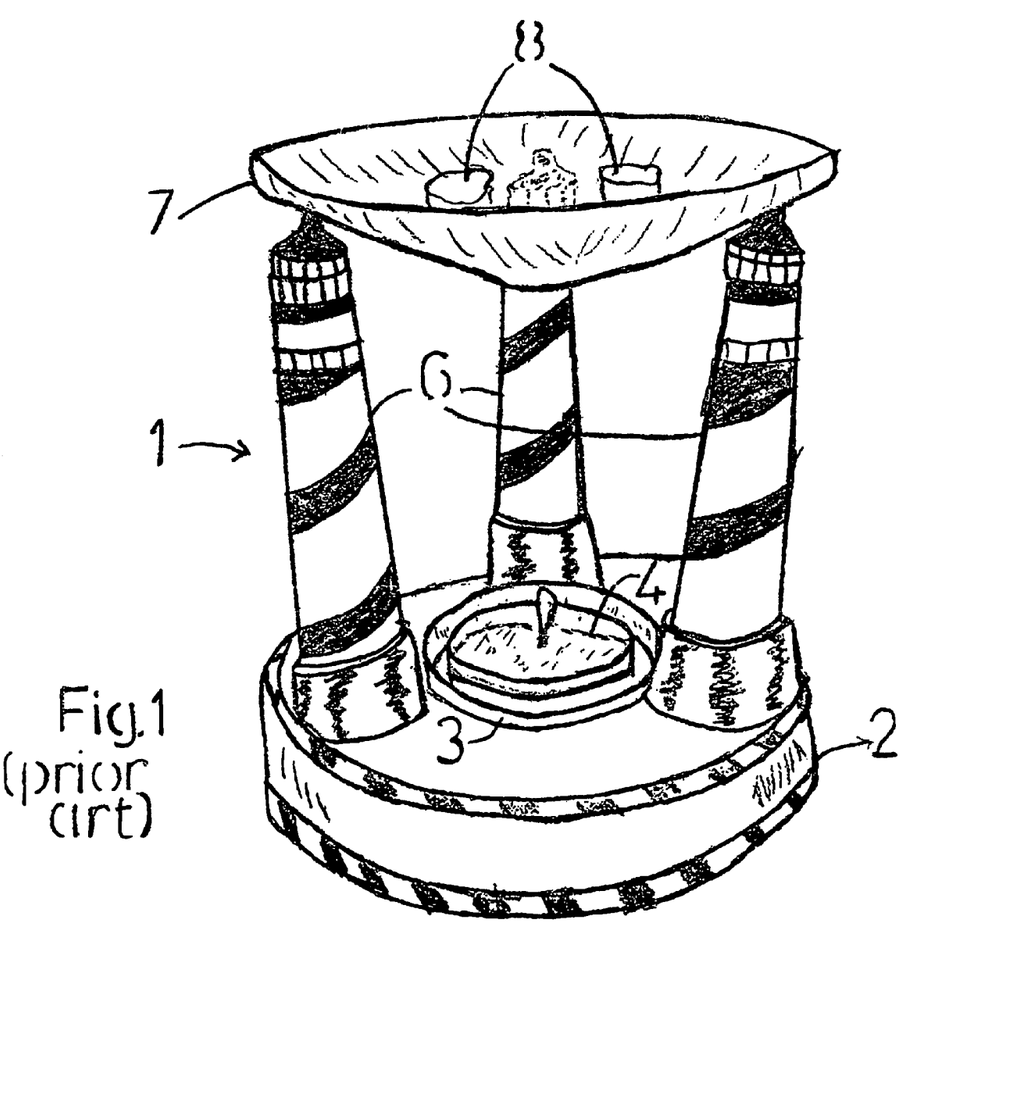
FIG. 1 is an isometric view of a prior art stand device used for heating aromatherapy formulated waxes.
Figure 2A:
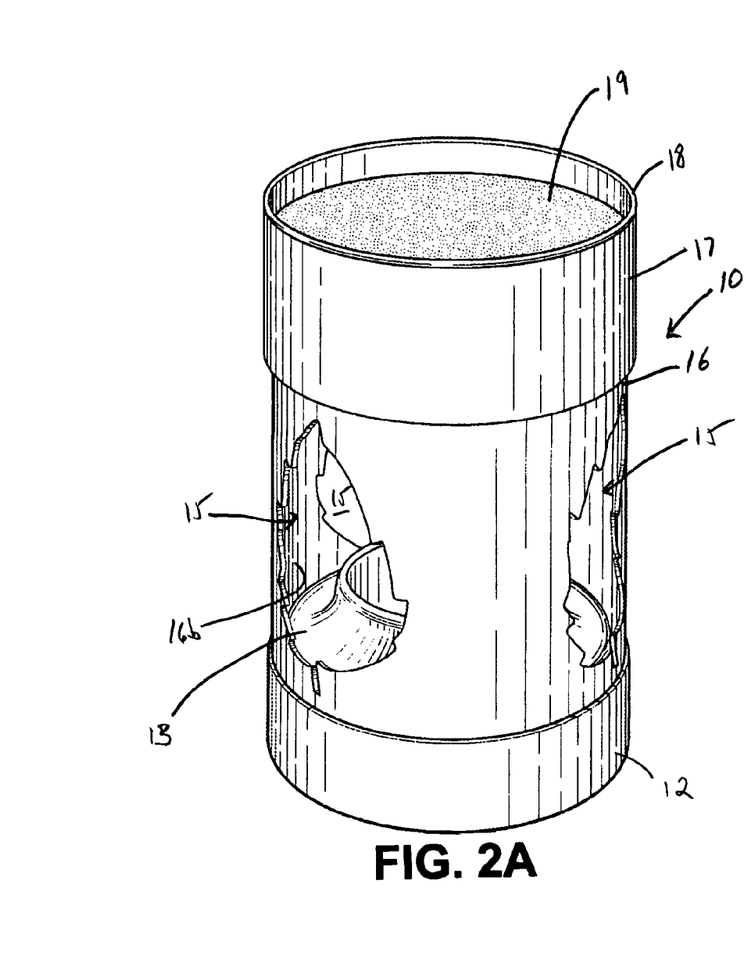
FIG. 2A is an isometric view of the substance heating container of the present invention with controlled heat.
Figure 2B:
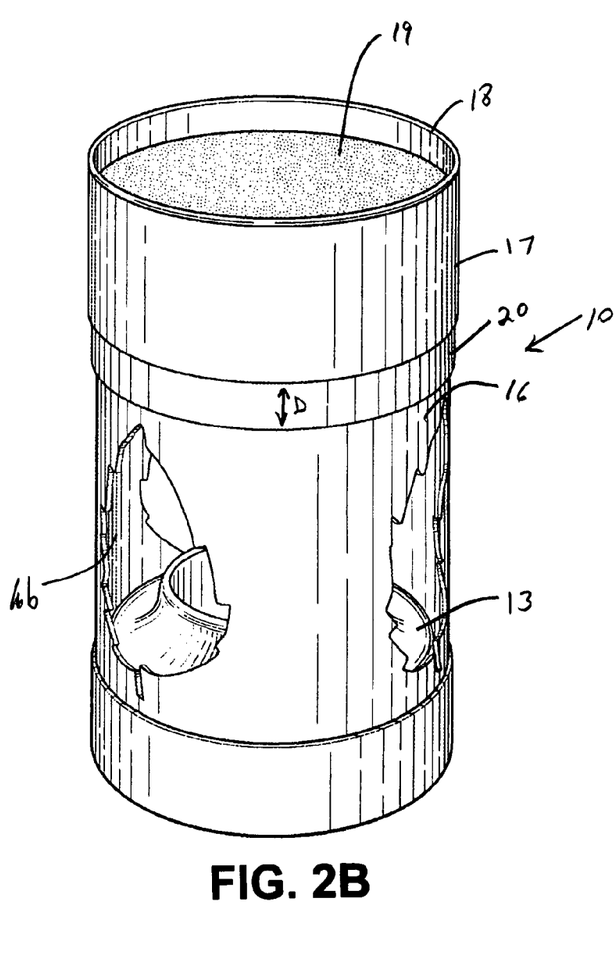
FIG. 2B is the container of FIG. 2A with the top being extended to reduce the equilibrium temperature.
Figure 3:
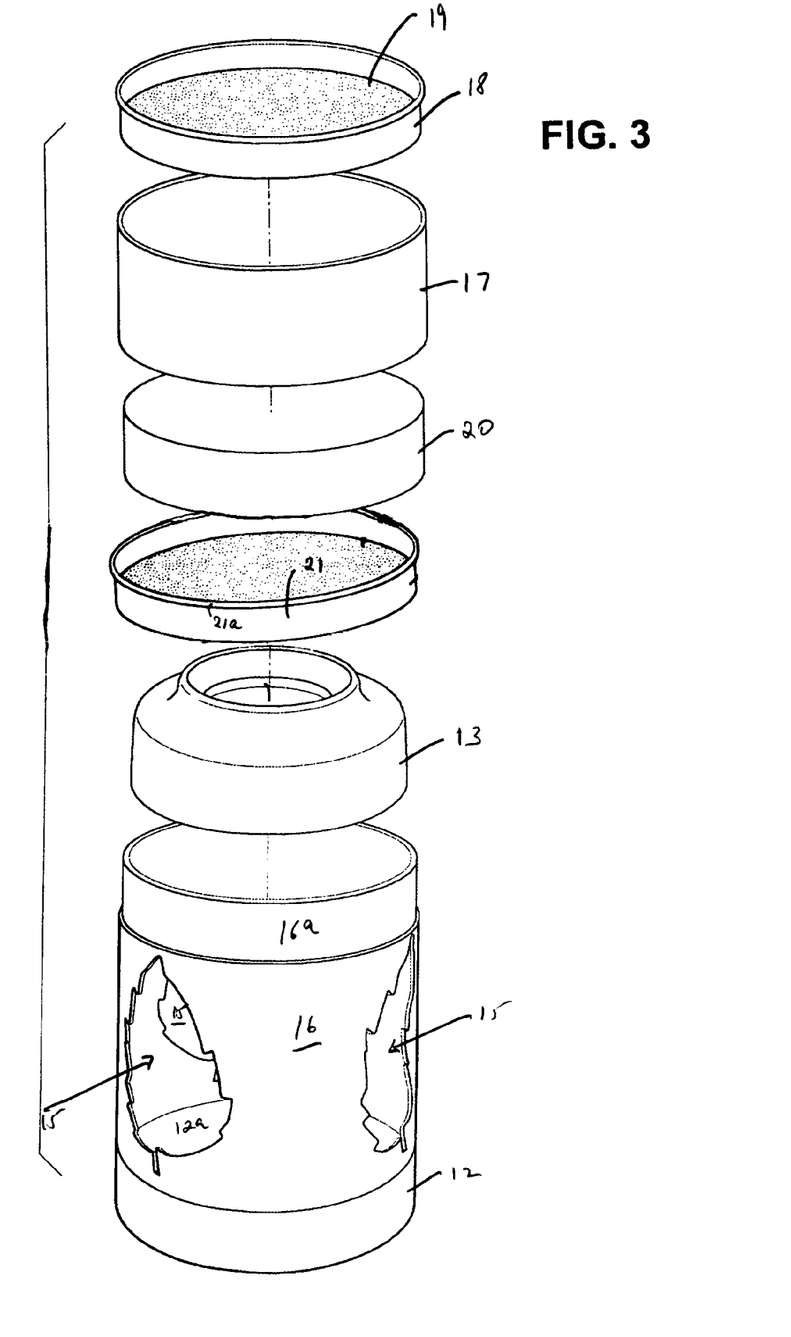
FIG. 3 is an exploded view of the container of FIGS. 2A and 2B.
Figure 4:
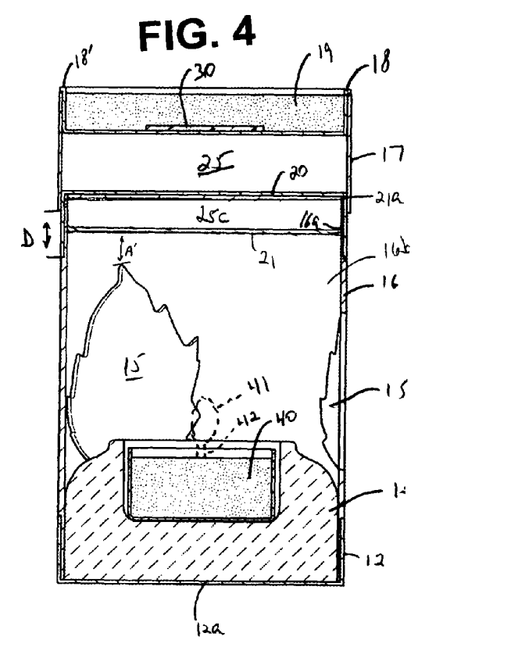
FIG. 4 is a cross section view of the container of FIG. 2A taken along line 4-4.

With reference to the drawings, in FIG. 1, a commercially available and representative aromatherapy wax heating device 1 is shown with a base 2, and three identical miniature ceramic lighthouses 6 (the lighthouses are simply decorative structural support members) which support glass heating dish 7. An aromatherapy wax material is placed in the heating dish 7. The base 2 supports a glass tea light holder 3 into which tea light 4 is placed. The flame of tea light 4 heats the heating dish 7 with aromatic wax 8 being melted therein after a period of time. Since the sides of the device 1 are essentially open, considerable time is needed for the wax to melt and provide the desire aroma. Heating thereafter continues without any control.

Heating device 10 of the present invention (configured to be suitable for skin therapy with described modification adaptations for aromatherapy use) is shown in FIGS. 2A, 2B, 3 and 4 with an aluminum cap base 12 fitted on di-electric flameproof paper tube 16. The cap base 12 or any other bottom closure is sufficiently press fitted to the paper tube 16 to support the standard glass tea light holder 13, which, in addition to holding the tea light heat source also provides weight ballast to the device to help prevent accidental tipping. The base 12 is removeable to provide a more preferred mode of candle placement into the container.

The paper tube 16 is shown as being apertured with three decorative leaf shaped apertures 15 circumferentially and equidistantly spaced on the tube. The apertures provide controlled venting of the heat generated by the flame 41 (shown in dotted line outline in FIG. 4) of tea light 40. The three apertures shown are adapted for use with skin therapy applications and a lower equilibrium temperature, whereas the same structure with two apertures and a slightly longer distance between the flame 40 and top cap 21 is suitable for the higher temperature aromatherapy applications. As more clearly seen in FIG. 4, top cap tin (tin plated steel) 21 is fitted onto thinned recess 16a of paper tube 16 with lip 21a and top cap aluminum closure 20 is fitted into the thinned recess 16a to form partially insulating air pocket 25c. The cap closure is adhered to the tube 16 in order to prevent it from being dislodged. Lighting of the tea light 40 is effected through one of the apertures 15. Wick 42 (shown in dotted line outline) is variable in width and material (cotton or cotton with paper) to provide additional parameter control of the heat as well as the composition of the tea light. The device 10 is sized as shown to accommodate a lower heat generating soy based tea light. Variations in size, aperture configuration and number, etc., may be made to accommodate paraffin wax tea lights which generate higher heat. Cap 21 is made of tin coated steel which provides more stability and resistance to heat warpage since it is directly exposed to the candle flame. Cap 18, when used for skin therapy materials, is comprised of an inert skin acceptable metal container such as aluminum.

Open ended paper tube extension member 17 is tightly but slidingly fit on cap closure 20 with cap 18 being fitted into the open upper end of tube extension member 17 (preferably sealingly adhered to provide an air tight seal). Lip 18a of the cap 18 fits on and is supported by the edge of the tube extension member 17. Member 17 is sized such that there is a spacing between the bases of caps closure 20 and cap 18, with another air volume 25. Distance D is the extent to which the bases can be moved relative to each other by sliding tube 17 over cap closure 20 with concomitant change in air volume 25 and insulation effect with variation in achieved equilibrium temperature. Cap closure 20 is fixed into position to prevent dislodging which may be effected by movement of the sliding tube 17.

Figure 6A:
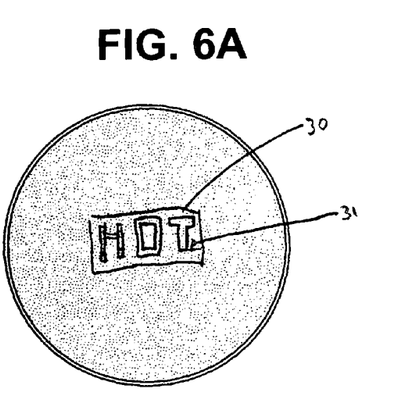
FIGS. 6A and 6B depict the heating indicia of wax in a safely warmed state and a too hot state respectively.
Figure 6B:
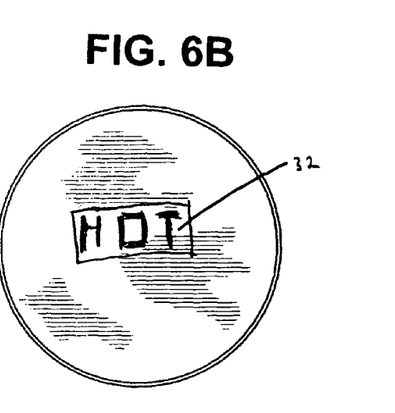
Figure 7:
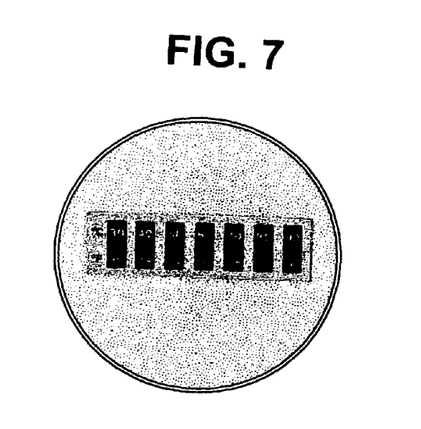
FIG. 7 depicts heating indicia in the form of a heat sensitive temperature range grid.

Cap 18 contains a material 19 which is to be heated such as a soy based wax for skin therapy. The cap 18 also contains heat sensitive indicia material such as liquid crystal materials which change color at very specific predetermined temperatures. As shown in FIGS. 6A and 6B, when the wax material 19 melts and becomes nearly transparent the indicia word HOT becomes visible in outline form. When the temperature reaches an uncomfortable temperature such as 140° F. the word turn dark as shown in FIG. 6B. The user can then lower the usable temperature by moving cup 18 away from the flame. Cold ambient air is immediately drawn in and the temperature drops quickly (a partial vacuum being formed facilitates this). In the embodiment shown in FIG. 7, actual temperature ranges can be detected and controlled as shown as the different ranges change in appearance, in a commercially available embodiment the temperature is indicated by color (black-not in range, green-lower range value temperature and blue-higher range value. Liquid crystal indicators are for example available from Liquid Crystal Sources in Glenview, Ill.

Prior to use, sliding tube 17 fits loosely and settles into the lowest position. As heat is generated during use, metal cap closure 20 expands slightly whereas the paper tube does not, thereby activating its use by providing a friction engagement to permit holding movement and positioning of the tube 17 with cup 18, as desired.

Figure 5:
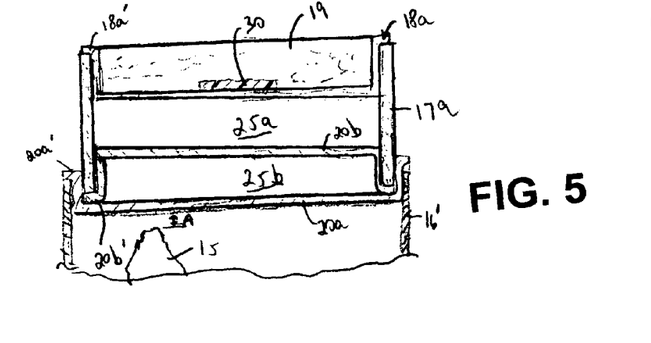
FIG. 5 is a cross section view of a second embodiment of the closure section of the container of FIGS. 3 and 4.

In the embodiment shown in FIG. 5, the movable cup arrangement is replaced with a tin cup 20a with lip 20a' which is fitted on the end of paper tube 16'. The base of cup 20a is closely distanced from the top of the apertures 15 by a distance A, to minimize accumulated heat. Paper tube extension member 17a is closed fitted within cup 20a and cup 18a is fitted into the open upper end of extension member 17a as with the first embodiment shown in FIGS. 2a, 2B, 3 and 4 with the same contained wax and liquid crystal indicia. Air volume 25a is formed to provide a partially insulating and temperature controlling means.

As shown in FIG. 5, if desired, a second air volume 25b may be formed by the inverted insertion of cup 20b, to provide further equilibrium temperature control.

Paper tube 16 is provided with a metallic foil 16b as an inner lining. The foil provides an aesthetic glow with a reflection of the candle light contained therein which appears through the apertures 15. In addition the foil reflects heat back to the candle or tea light from the exterior whereby melting of the candle is more uniform, i.e., edge to edge, without need to use a larger wick size to this effect. Enhanced temperature control and more efficient use of the candle results, independent of the container closure.

It is understood that the above description and drawings are illustrative of the present invention and are not to be considered limitations thereof. Changes may be made in wax formulation as well as the use of non wax materials requiring heating. Similarly changes in structure and materials may be made to the heating device without departing from the scope of the present invention as defined in the following claims.

What is claimed is:

1. A non-thermostatic heating device comprising an insulative flame retardant container adapted to contain a heating source and having a lower closed end, and an upper end comprised of means to hold a material requiring melting or heating, thereon, said device further comprising means for non-thermostatic temperature control to maintain a temperature of the material requiring melting or heating within a predetermined range with continued heating by said heating source, wherein said means for non-thermostatic temperature control means comprises one or more partial heat insulation and heat conduction members positioned between the heating source said means to hold and the material requiring melting or heating, wherein the one or more partial heat insulation and partial heat conduction members provide a top closure for the insulative flame retardant container and wherein said members comprise one or more fully enclosed air volumes wherein the device further comprises a imperforate member configured to vary the fully enclosed air volume of at least one of the fully enclosed air volumes to thereby controllably vary an existing temperature to a desired temperature in the predetermined range.

2. The non-thermostatic heating device of claim 1, wherein the insulative flame retardant container is comprised of flame retardant paper.

3. The non-thermostatic heating device of claim 2, wherein said heating source comprises a tea light comprised of a soy wax.

4. The non-thermostatic heating device of claim 1, wherein the material is in thermal contact with visible temperature indicating indicia.

5. The non-thermostatic heating device of claim 1 wherein said member configured to controllably vary the volume is usably activated with concomitant heating of said heat insulation and heat conduction members.

6. The non-thermostatic heating device of claim 5, wherein said member configured to controllably vary the volume comprises elements configured to form a partial vacuum within said volume to draw in cooling air into said volume.

7. The non-thermostatic heating device of claim 1, wherein the volume is varied to provide the predetermined range as being between 125 to 135° F.

8. The non-thermostatic heating device of claim 7, wherein said material is adapted for use as a skin application wherein the top closure is comprised of at least one member which maintains structural integrity when in direct contact with heat of said heating source and one member not in direct contact with said heat but in direct contact with said skin application materials with said member in direct contact with the skin application material being comprised of an acceptable container material for said skin application material.

9. The non-thermostatic heating device of claim 1, wherein the volume is varied to provide the predetermined range as being between 120 and 180° F.

* * * * *